US008377887B1

(12) United States Patent
Chang et al.

(10) Patent No.: US 8,377,887 B1
(45) Date of Patent: Feb. 19, 2013

(54) METHODS OF REDUCING HYPOXIC STRESS IN A MAMMAL BY ADMINISTERING SOLUBLE P-SELECTIN

(76) Inventors: Hsin-Hou Chang, Taipei (TW); Der-Shan Sun, Taipei (TW)

( * ) Notice: Subject to any disclaimer, the term of this patent is extended or adjusted under 35 U.S.C. 154(b) by 1691 days.

(21) Appl. No.: 11/648,166

(22) Filed: Dec. 29, 2006

Related U.S. Application Data

(63) Continuation-in-part of application No. 10/902,489, filed on Jul. 29, 2004, now abandoned.

(30) Foreign Application Priority Data

Jul. 29, 2003 (TW) .............................. 92120683 A

(51) Int. Cl.
*A61K 38/00* (2006.01)
*A61K 38/16* (2006.01)
*C07K 14/705* (2006.01)
*A61P 7/00* (2006.01)

(52) U.S. Cl. ...................... 514/19.1; 514/13.5; 514/21.2
(58) Field of Classification Search .................. None
See application file for complete search history.

(56) References Cited

U.S. PATENT DOCUMENTS

2002/0031508 A1    3/2002    Wagner et al.

OTHER PUBLICATIONS

Rieger R, et al. Glossary of Genetics, 5th ed. Springer-Verlag, New York, pp. 16-17, 1991.*
Andre, P., et al. "Pro-coagulant state resulting from high levels of soluble P-selectin in blood." PNAS (2000) vol. 97, No. 25, pp. 13835-13840.
Kader A, Krauss WE, Onesti ST, Elliott JP, Solomon RA. Chronic cerebral blood flow changes following experimental subarachnoid hemorrhage in rats. Stroke; a journal of cerebral circulation 1990;21:577-81.
Subramaniam M, Frenette PS, Saffaripour S, Johnson RC, Hynes RO, Wagner DD. Defects in hemostasis in P-selectin-deficient mice. Blood 1996;87:1238-42.
Andre P, Hartwell D, Hrachovinova I, Saffaripour S, Wagner DD. Pro-coagulant state resulting from high levels of soluble P-selectin in blood. Proceedings of the National Academy of Sciences of the United States of America 2000;97:13835-40.
Gutierrez G, Reines HD, Wulf-Gutierrez ME. Clinical review: hemorrhagic shock. Crit Care 2004;8:373-81.
Martel MJ, MacKinnon KJ, Arsenault MY, Bartellas E, Klein MC, Lane CA, et al. Hemorrhagic shock. Journal of obstetrics and gynaecology Canada : JOGC=Journal d'obstetrique et gynecologie du Canada : JOGC 2002;24:504-20; quiz 21-4.
Shohet, Ralph V., et al., "Keeping the engine primed: HIF factors as key regulators of cardiac metabolism and angiogenesis during ischemia", J. Mol Med (2007) 85:1309-1315.
Chi, Neil C., et al., "Molecular determinants of response to myocardial ischemia/reperfusion injury: focus on hypoxia-inducible and heat shock factors", Cardiovascular Research 61 (2004), 437-447.
Walshe, Tony E., et al., "The Role of Hypoxia in Vascular Injury and Repair", Annu. Rev. Pathol Mech. Dis. 2008: 3:615-643.
Trayhurn, Paul, et al., "HIF-1 α protein rather than mRNA as a marker of hypoxia in adipose tissue in obesity: focus on Inflammation is associated with a decrease of lipogenic factors in omental fat in women", Am J. Physiol Regul Ingegr Comp Physiol 295: R1097, 2008.
Vukovic, Vojislav, et al., "Hypoxia-inducible Factor-1α is an Intrinsic Marker for Hypoxia in Cervical Cancer Xenografts", Cancer Research 61, 7394-7398, Oct. 15, 2001.
Semenza, Gregg L., "Hypoxia-inducible factor 1: Regulator of mitochondrial metabolism and mediator of ischemic preconditioning", Biochimica et Biophysica Acta 1813 (2011) 1263-1268.
Trollman, Regina, et al., "The role of hypoxia-inducible transcription factors in the hypoxic neonatal brain", Brain & Development 31 (2009) 503-509.
Kaluz, Stefan, et al., Transcriptional control of the tumor- and hypoxia-marker *carbonic anhydrase 9*: A one transcription factor (HIF-1) show?, Biochimica et Biophysica Acta 1795 (2009) 162-172.

* cited by examiner

*Primary Examiner* — Robert Landsman
(74) *Attorney, Agent, or Firm* — Ladas & Parry LLP

(57) ABSTRACT

The present invention provides a use of soluble P-selectin in treating systemic hemorrhagic conditions, stabilizing blood pressure, and protecting hypoxic/ischemic tissues. Also provided is a use of anthrax lethal toxin in treating thrombotic conditions.

4 Claims, 8 Drawing Sheets

FIG. 2

METHODS OF REDUCING HYPOXIC STRESS IN A MAMMAL BY ADMINISTERING SOLUBLE P-SELECTIN

This application is a continuation-in-part of application Ser. No. 10/902,489 filed Jul. 29, 2004 (now abandoned) and claims the benefit thereof and incorporates the same by reference.

FIELD OF THE INVENTION

The present invention relates to novel uses of soluble platelet-selectin (P-selectin) in treating of systemic hemorrhagic conditions, stabilizing blood pressure, reducing the hypoxic/ischemic stress and protecting hypoxic/ischemic tissues.

BACKGROUND OF THE INVENTION

Hemorrhagic conditions are diverse in classification, and their pathogenic factors are complicated, including such as abnormality in the structure of vascular walls or connective tissues, abnormality in the amount or function of platelets, abnormality in coagulant factors, over-fibrinolysis, and circulating anti-coagulant substances. Based on the involvement of inheritance, hemorrhagic conditions can be divided into inherited and non-inherited hemorrhagic conditions. Inherited hemorrhagic conditions, such as hemophilia, are resulted from mutations in the coagulant factors, which result in the loss or decrease of coagulation ability. Clinically, most hemorrhagic conditions are non-inherited hemorrhagic conditions, including internal and external traumatic hemorrhage, hemorrhage resulted from insufficient ingestion of nutrition or vitamin K, hemorrhage resulted from gastric or intestinal ulcer, hemorrhage resulted from infectious diseases, hemorrhage resulted from medical behaviors, intrapartum hemorrhage, abnormality in the hematopoietic system, disorders in liver functions, hemorrhage resulted from autoimmune diseases, dengue hemorrhagic fever, hemorrhagic venom attack, anthrax, bacteremia, and hemorrhage resulted from cancer.

Except for traumatic hemorrhage, the present medical treatments have no effect on systemic hemorrhea. The presently known coagulant drugs (such as anti-fibrinolysis agents) are only suitable for treating local hemorrhage. Such coagulant drugs form small thrombus in vivo quickly, and thus often result in side effects such as myocardial infarction and cerebral stroke. Therefore, there exists no suitable and safe systemic haemostatic drugs without side effects.

P-selectin is a member of the selectin family localized in the membranes of α-granules of platelets and the Weibel-Palade bodies (WP bodies) of endothelial cells. Endothelial cells quickly express P-selectin when stimulated by thrombin or histamine. A soluble form of P-selectin (soluble P-selectin; sP-selectin) can be found in the plasma as a circulating protein. A soluble P-selectin molecule, which exists as a monomer in the blood, is 3 kDa smaller than a P-selectin molecule, which exists as an oligomer on a membrane. The soluble P-selectin of healthy individuals originates from the alternatively spliced form found in endothelial cells and platelets (Johnston, G. I. et al., 1990, J. Biol. Chem. 265, 21381-21385).

A previous study showed that the plasma level of soluble P-selectin can be viewed as a useful tool for anticipating thrombotic consumptive platelet disorders (Smith, A. et al., 1999, Throm. Haemost. 82, 1593-1599). Blann, A. D. and Lip, G. Y. indicated that the biological functions of the soluble P-selectin circulating in the blood are unclear (J. Clin. Endocrinol. Metab. (2000) 85, 1745-1747). A Follow-up study utilizing a test determining the plasma clotting time found that soluble P-selectin injected into mice can promote coagulation (Patrick Andre et al., 2000, PNAS Vol. 97, No. 25, 13835-13840). Said study only described the molecular mechanism and local hemorrhage, and inferred that soluble P-selectin may relate to coagulation disorders. However, said study did not indicate that soluble P-selectin can be used in the treatment of systemic hemorrhagic conditions.

Further studies indicated that the plasma soluble P-selectin level of patients suffering from acute myocardial infarction (AMI) and unstable angina pectoris increases significantly (Meral Kayikcioglu et al., Int. J. Cardiol., 2001, 79: 223; Enver Atalar et al., Int. J. Cardiol., 2001, 78: 69). However, said literatures did not suggest anything regarding the treatment of systemic hemorrhagic conditions, either.

In view of the above, no literature disclosed or even suggested the novel use of P-selectin in the treatment of systemic hemorrhagic conditions.

SUMMARY OF THE INVENTION

The present invention provides a method of treating systemic hemorrhagic conditions in a mammal, which comprises administrating to said mammal a pharmaceutical composition comprising soluble P-selectin and a pharmaceutically acceptable carrier.

The present invention also provides a method of stabilizing blood pressure in a mammal, which comprises administrating to said mammal a pharmaceutical composition comprising soluble P-selectin and a pharmaceutically acceptable carrier.

The present invention also provides a method of reducing hypoxic stress in a mammal, which comprises administrating to said mammal a pharmaceutical composition comprising soluble P-selectin and a pharmaceutically acceptable carrier. According to one embodiment of the present invention, the soluble P-selectin can be used in the manufacture of a medicament for protecting hypoxic/ischemic tissues.

The present invention also provides a method of treating a condition in need of the inhibition of thrombosis or coagulation in a mammal, which comprises administrating to said mammal a pharmaceutical composition comprising an anti-P-selectin antibody or P-selectin ligand-1 (PSGL-1) and a pharmaceutically acceptable carrier.

The present invention also provides a method of treating thrombotic conditions in a mammal, which comprises administrating to said mammal a pharmaceutical composition comprising anthrax lethal toxin and a pharmaceutically acceptable carrier.

BRIEF DESCRIPTION OF THE DRAWING

FIGS. 2A-2B show the data obtained in mouse protection test. The data in FIG. 2A represent the protection on mice treated with hemorrhagic snake venoms by soluble P-toxin. The symbol "---○---" means snake venom of *Crotalus atrox*+Recombinant Soluble P-selectin (rP-sel); the symbol "-▼-" means snake venom of *Crotalus adamanteus*+Recombinant Soluble P-selectin (rP-sel); the symbol "-▽-" means snake venom of *Crotalus atrox*; and the symbol "-■-" means snake venom of *Crotalus adamanteus*. The data in FIG. 2B represent the protection on mice treated with anthrax lethal toxin by soluble P-toxin, the symbol "-●-" means Anthrax Lethal Toxin (LeTx); the symbol "---○---" means Anthrax Lethal Toxin (LeTx)+Recombinant Soluble P-selectin (rP-sel); the symbol "-▼-" means Anthrax Lethal Toxin (LeTx)+Control Immunoglobulin (IgG); and the symbol "∇" means Anthrax Lethal Toxin (LeTx)+Recombinant Soluble P-selectin (rP-sel)+Anti-P-selectin Antibody (Anti-P-sel).

DETAILED DESCRIPTION OF THE INVENTION

Figure 1:
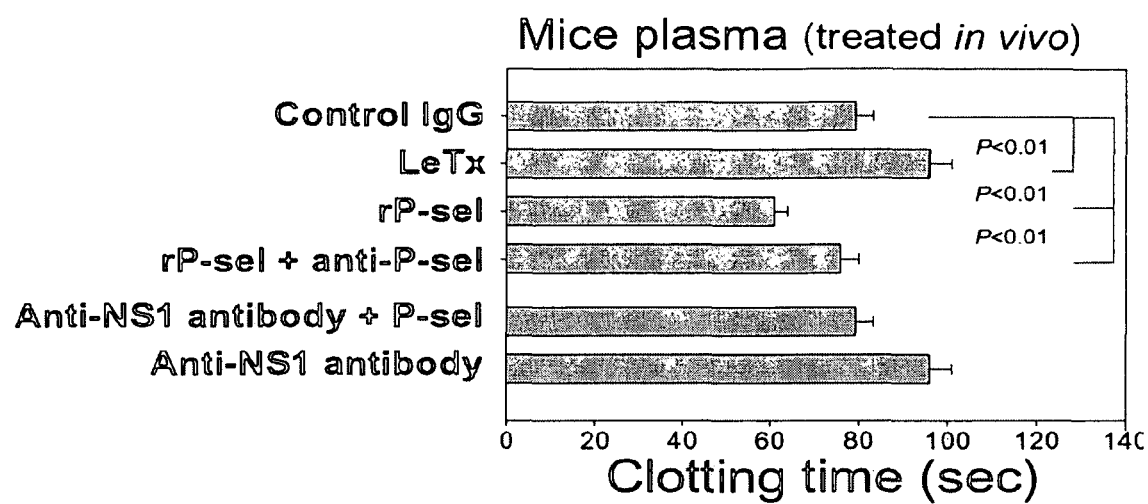
FIG. 1 shows the data obtained in the plasma clotting test. The bars in the figure represent, from top to bottom: Control Immunoglobulin (IgG); Anthrax Lethal Toxin (LeTx); Recombinant Soluble P-selectin (rP-sel); Recombinant Soluble P-selectin (rP-sel)+Anti-P-selectin Antibody (Anti-P-sel); Anti-dengue Non-structural Protein 1 Antibody (Anti-NS1 Antibody)+P-selectin; and Anti-dengue Non-structural Protein 1 Antibody (Anti-NS1 Antibody).

Currently, there is no effective drug for systemic hemorrhagic conditions which does not have a risk of thrombosis. The current therapies are mostly supporting treatments. There is no better way to treat systemic hemorrhage. The present invention provides the novel use of soluble P-selectin in the treatment of systemic hemorrhagic conditions. Said soluble P-selectin can effectively treat hemorrhagic conditions, particularly anthrax, dengue hemorrhagic fever and bacteremia, and does not induce the side effect of thrombosis. In addition, the soluble P-selectin of the present invention can also be used in stabilizing blood pressure and reducing ischemic/hypoxic stress.

Novel Use of Soluble P-Selectin in Treating Systemic Hemorrhagic Conditions

The present invention provides a method of treating systemic hemorrhagic conditions in a mammal, which comprises administrating to said mammal a pharmaceutical composition comprising soluble P-selectin and a pharmaceutically acceptable carrier.

According to the present invention, soluble P-selectin provides a novel use in the treatment of systemic hemorrhagic conditions. The present inventors unexpectedly found that soluble P-selectin significantly promotes coagulation, but does not induce thrombosis, which results in myocardial infarction and cerebral stroke. Therefore, the soluble P-selectin of the present invention is effective in the treatment of systemic hemorrhagic conditions, and does not have undesirable side effects.

In particular, the soluble P-selectin of the present invention is useful in the treatment of dengue hemorrhagic fever, hemorrhagic snake venoms, anthrax and hemorrhagic conditions in bacteremia. Preferably, the soluble P-selectin of the present invention is useful in the treatment of dengue hemorrhagic fever, hemorrhagic snake venoms and anthrax. Dengue hemorrhagic fever is a systemic hemorrhagic condition resulted from multiple infections of dengue viruses. At the first time of dengue virus infection, most patients only exhibit the symptoms of common colds, and their lives are not threatened. However, after multiple infections of dengue viruses, a specific ratio of patients exhibits life-threatening systemic hemorrhagic conditions. Dengue non-structural protein 1 (NS1) can induce autoimmune antibodies of the host, and the valence of the antibodies increases due to multiple dengue virus infection. Such autoimmune antibodies slow the coagulation rate and result in other possible vascular disorders. Hemorrhagic viper bites are common outdoor risks in Taiwan and other tropical regions. The only effective treatment is the injection of anti-venom serum. However, the species of vipers are numerous. To treat venom poison, specific anti-venom serum must be prepared for each species of vipers. This is a burden which cannot be easily achieved in remote areas. Anthrax, on the other hand, is a disease induced by *Becillus anthracis* infection. The anthrax lethal toxin produced by *Becillus anthracis* is the major virulence factor. It has been found that most of the patients died from anthrax exhibit severe internal hemorrhage. The present inventors surprisingly found that soluble P-selectin has a good effect on the treatment of dengue hemorrhagic fever, hemorrhagic snake venoms and anthrax, and does not have any side effect.

Novel Use of Soluble P-Selectin in Stabilizing Blood Pressure and Reducing Hypoxic/Ischemic Stress The present invention provides a method of stabilizing blood pressure in a mammal, which comprises administrating to said mammal a pharmaceutical composition comprising soluble P-selectin and a pharmaceutically acceptable carrier. In addition, it also provides a method of reducing hypoxic stress in a mammal, which comprises administrating to said mammal a pharmaceutical composition comprising soluble P-selectin and a pharmaceutically acceptable carrier.

The present inventors also found that soluble P-selectin is very effective in stabilizing blood pressure and reducing the expression level of HIF-1α. According to one embodiment of the invention, the soluble P-selectin is effective in protecting hypoxic/ischemic tissues, and thus it is helpful in alleviating relevant symptoms and reducing the death rate.

The invention surprisingly found that both before and after hemorrhage/reperfusion procedures, the soluble P-selectin significantly maintaining the blood pressure in a relatively higher level. We sutured all wounds of blood vessel after the blood collection at the beginning to ensure there is no further bleeding during the later hemorrhage/reperfusion procedures. In view that there is no further bleeding in these experimental mice, the amelioration effect of rP-sel treatment is not contributed by its ability to enhance coagulation.

After a further analysis, it is unexpectedly found that the soluble P-selectin can reduce the expression levels of HIF-1α, which indicates a reduced hypoxic stress. Thus, the soluble P-selectin also prevent from ischemia- and hypoxia-induced damages, and whence prolonged the surviving time of ischemic animal. According to the invention, the term "Ischemia condition" refers to injury-, surgery-, infection-, genetic factor-, snake bite with hemorrhage venom, or other pathophysiological situations that resulting blood-lost.

Novel Use of Anti-P-Selectin Antibodies and P-Selectin Ligand-1 (PSGL-1)

The invention surprisingly found that anti-P-selectin antibodies or P-selectin ligand-1 (PSGL-1) has an efficacy in the treatment of a condition in need of the inhibition of thrombosis or coagulation. According to the invention, Falati, S. et al., Fernandes, L. S. et al., Thatte, A., Ficarro et al. and Theoret, J. F. et al. demonstrated that the recombinant P-sel (rP-sel), recombinant PSGL-1 (rPSGL-1) and anti-P-sel antibody (anti-P-sel-Ig) exert their blocking activities and suggested that their roles might be similar in vivo (J Exp Med 197:1585-1598; Thromb Res 111:171-177; J Leukoc Biol 72:470-477; and J Pharmacol Exp Ther 298:658-664). Contrary to the prior art, the invention unexpectedly found that only rP-sel could ameliorate the hemorrhage symptoms and mortality. However, rPSGL-1 and anti-P-sel-Ig greatly enhance the hemorrhage and mortality.

Soluble P-Selectin and Pharmaceutical Composition Thereof

According to the present invention, the term "soluble P-selectin" comprises naturally occurring soluble forms of P-selectin and recombinant forms thereof, or polymorphic or allelic variants or other isoforms thereof. The term also comprises modified or unmodified soluble P-selectin, such as glycosylated or non-glycosylated forms. Previous studies reveal that soluble P-selectin may originate from activated platelets or endothelial cells. However, the functions of soluble P-selectin and its relationship with platelets are not very clear to persons of ordinary skills in the art. Unexpectedly, the present inventors found that soluble P-selectin provides an excellent effect on the treatment of systemic hemorrhagic conditions. According to the present invention, any forms of soluble P-selectin suitable for treating systemic hemorrhagic conditions can be used in the present invention. Preferably, the soluble P-selectin of the present invention is naturally occurring soluble P-selectin or recombinant soluble P-selectin. According to the present invention, soluble P-selectin can be easily obtained by persons of ordinary skills in the art, such as being isolated from a natural source, purchased from a commercial source, or synthesized with molecular biological techniques.

The soluble P-selectin of the present invention can be prepared into a pharmaceutical composition with a pharmaceutically acceptable carrier. Except for soluble P-selectin and the carrier, said composition may further comprise a diluent, filler, salt, buffer, stabilizing agent, solubilizing agent, and other substances known in the art. The term "pharmaceutically acceptable" refers to non-toxic substances which do not interfere with the biological activity of the active ingredient. The properties of the carrier used in the soluble P-selectin pharmaceutical composition of the present invention are determined based on the administration route. The pharmaceutical composition of the present invention may also comprise a coagulant known in the art, such as vitamin K and anti-fibrinolysis agents.

Administration of Soluble P-selectin

To practice the present invention, a therapeutically effective amount of the soluble P-selectin or pharmaceutical composition of the present invention can be administered to a mammal, including a human or non-human mammal, suffering from hemorrhagic conditions. According to the present invention, the administration of the soluble P-selectin or pharmaceutical composition of the present invention can be carried out by various ordinary ways, such as intravenous administration. When administered in a liquid form, liquid carriers, such as water, saline, and animal or plant oils, may be added. The liquid-form pharmaceutical composition comprises 0.5% to 90% by weight of soluble P-selectin, preferably 1% to 50% by weight of soluble P-selectin.

When a therapeutically effective amount of soluble P-selectin is administered via intravenous injection, the soluble P-selectin is in the form of a parenterally acceptable aqueous solution. The pH, isotonicity, stability and similar conditions to be considered in the preparation of such parenterally acceptable aqueous solution are technology and knowledge known in the art. Except for soluble P-selectin, a preferable pharmaceutical composition for intravenous injection may comprise an isotonic solvent known in the art. The pharmaceutical composition of the present invention may also comprise a stabilizing agent, preservative, buffer, anti-oxidant or other additives known to persons of ordinary skills in the art. The time of intravenous injection treatment with the pharmaceutical composition of the present invention is determined based on the severity of the disease to be treated and the conditions of individual patients. A doctor shall determine the adequate amount of time of intravenous injection treatment with the pharmaceutical composition of the present invention.

The amount of soluble P-selectin in a pharmaceutical composition according to the present invention is determined based on the properties and severity of the disease to be treated and the properties of the treatment previously applied to the patient. A doctor shall determine the amount of soluble P-selectin based on the conditions of individual patients. Regarding the various pharmaceutical compositions for practicing the present invention, it is expected that about 0.1 ng to about 100 mg of soluble P-selectin should be administered per kilogram of bodyweight.

Novel Use of Anthrax Lethal Toxin in Treating Thrombotic Conditions

The present invention also provides a method of treating thrombotic conditions in a mammal, which comprises administrating to said mammal a pharmaceutical composition comprising anthrax lethal toxin and a pharmaceutically acceptable carrier. Thrombotic conditions can result in complications such as myocardial infarction and cerebral stroke. Such cardiovascular diseases resulted from thrombosis almost rank among the top ten causes of death. Frequently—used anti-thrombotic drugs include platelet inhibitors, tissue plasminogen activator (tPA), urokinase-type plasminogen activator (uPA), and streptokinase (SK). However, there is still lack of very effective anti-thrombotic drugs. The present inventors surprisingly found that anthrax lethal toxin can effectively inhibit platelet aggregation, and thereby can be used as an anti-thrombotic drug.

According to the present invention, the term "anthrax lethal toxin" comprises naturally occurring anthrax lethal toxin and recombinant forms thereof, or polymorphic or allelic variants or other isoforms thereof. According to the present invention, any forms of anthrax lethal toxin suitable for treating thrombotic conditions can be used in the present invention. Preferably, the anthrax lethal toxin of the present invention is naturally occurring anthrax lethal toxin or recombinant anthrax lethal toxin. According to the present invention, anthrax lethal toxin can be easily obtained by persons of ordinary skills in the art, such as by isolating it from a natural source, purchased from a commercial source, or synthesizing it with molecular biological techniques.

According to the present invention, a therapeutically effective amount of the anthrax lethal toxin or pharmaceutical composition of the present invention can be administered to a mammal, including a human or non-human mammal, suffering from thrombotic conditions. According to the present invention, the administration of the anthrax lethal toxin or pharmaceutical composition of the present invention can be carried out in various ordinary ways, such as oral administration or intravenous injection, preferably intravenous administration. Preferably, it is expected that about 0.01 µg to 500 µg of the anthrax lethal toxin of the present invention should be administered for per kilogram of bodyweight.

The anthrax lethal toxin of the present invention can significantly inhibit platelet aggregation and reduce the risk of complications such as myocardial infarction and cerebral stroke.

EXAMPLE

Example 1

Plasma Clotting Test of Dengue Hemorrhagic Fever and Anthrax Lethal Toxin

In the plasma clotting test, the blood from C57BL/6J mice was centrifuged under 1,500×g for 25 minutes to obtain the "platelet-poor plasma" (PPP) of the mice. Equal volume of 20 mM $CaCl_2$ was added to the obtained plasma, and the change in absorbance resulted from coagulation was recorded under stirring (800 rpm) and 37° C. on an aggregometer (Model 600B, Ion-Trace, Stouffville, Canada), and the plasma clotting time was determined.

The following reagents were used in the plasma clotting test of this example: recombinant P-selectin-Ig Fc protein (purchased from R & D Systems Inc., Minneapolis, Minn., USA), as the source of P-selectin; dengue non-structural protein 1, as the dengue virus protein, which was obtained from the PCR-synthesized structural protein 1 gene of the Taiwan local strain PL046 of dengue virus type II (Chang et al., 2002, J. Infect. Dis. 186, 743-51); recombinant anthrax lethal toxin, as the anthrax lethal toxin, which is obtained from a DNA synthesized by the artificial gene synthesizing technique in combination with PCR technique, based on the DNA and protein information (AF065404 and NC_001496) obtained from NCBI Gene Bank, USA (Chang et al., 1993, Biochem. Biophys. Res. Commun. 190, 242-9).

The infusion of the anti-dengue non-structure protein 1 antibody (Anti-NS1 Antibody) and anthrax lethal toxin (LeTx) into the mice inhibited plasma clotting. As shown in FIG. 1, after 24-hour intravenous infusion of Anti-NS1 Antibody and LeTx, the plasma clotting time increased significantly, which implies that the clotting rate decreased. On the contrary, after 24-hour intravenous infusion of recombinant soluble P-selectin (rP-sel), the plasma clotting time decreased significantly, which implies that the clotting rate increased. However, if an anti-P-selectin antibody (Anti-P-sel) was added, the above effect of rP-sel was neutralized. In addition, after 24-hour intravenous infusion of Anti-NS1 Antibody together with soluble P-selectin, the plasma clotting time decreased significantly when compared to the infusion of Anti-NS1 Antibody.

As can be seen from the above results shown in FIG. 1, soluble P-selectin can promote the activation of in vivo coagulation mechanisms. In addition, the infusion of a therapeutic amount of soluble P-selectin alone does not harm the tested animals, but largely increases the coagulation efficiency. Therefore, soluble P-selectin is a very potent candidate of systemic styptic drug.

Example 2

Mouse Protection Test of Anthrax Lethal Toxin and Hemorrhagic Venoms

In the test of mouse protection by P-selectin, mice were first injected with the recombinant P-selectin-Ig protein, P-selectin+neutralizing monoclonal antibody, or control human immunoglobulin IgG (the dosages are all 1.2 µg/g). After 4 hours, the mice were intravenously injected with anthrax lethal toxin and hemorrhagic venoms. The time of death of the mice were observed. The sources of the recombinant P-selectin-Ig protein and anthrax lethal toxin are shown in Example 1. Venoms of *Crotalus atrox* and *Crotalus adamanteus* (purchased from Sigma, St. Louis, Mo., USA) were used as the hemorrhagic venoms.

Figure 2:
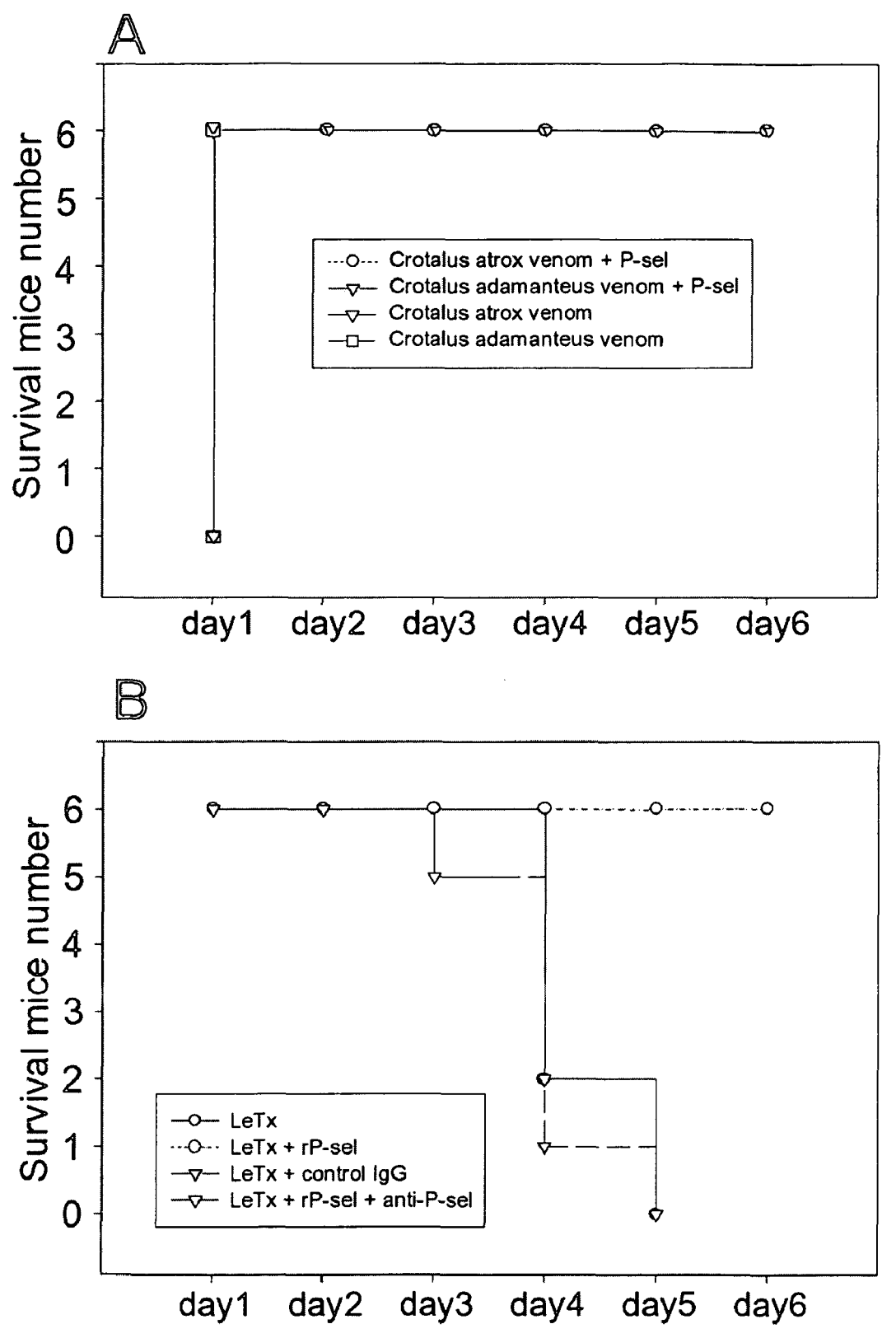

As shown in FIG. 2A, the injected venoms of *Crotalus atrox* and *Crotalus adamanteus* each resulted in the death of all the six mice (C57BL/6J) within 1 hour. However, the mice previously injected with recombinant soluble P-protein all survived for more than 3 months, which proves that soluble P-selectin provides protection against hemorrhage. The above test proves that the poisonous damage of hemorrhagic venoms can be treated with soluble P-selectin to avoid death (FIG. 2A). Therefore, soluble P-selectin may be developed into a single systemic anti-hemorrhagic-venom drug.

In addition, as shown in FIG. 2B, the injected anthrax lethal toxin (LeTx) resulted in the death of all the six mice (C57BL/6J) within 4-5 days. However, one of the mice previously injected with recombinant soluble P-protein died on the $8^{th}$ day, another died on the $18^{th}$ day, and the remaining four mice survived for more than 3 months. The above data proves that soluble P-selectin provides protection against hemorrhage. Moreover, it can be understood from the figure that the protection provided by soluble P-selectin can be neutralized by P-selectin-specific antibodies. Therefore, the above test shows that soluble P-selectin can reduce the number of deaths resulted from anthrax lethal toxin.

Example 3

Protection Test of Mice with Bacteremia

The reagents and method of the mouse protection test are as shown in Example 2. The bacteremia of mice was simulated by injecting $1\times10^8$ bacteria/g of *Escherichia coli* (*E. coli*) into the plasma of mice (C57BL/6J). As shown in Table 1, all the six mice injected with the *E. coli* solution died within 24 hours. However, the mice previously injected with recombinant soluble P-protein survived for two more days in average. Therefore, soluble P-selectin does provide mice with protection against bacteremia.

TABLE 1

| Treatment of Mice | Average Surviving Days |
| --- | --- |
| Injected with Soluble P-selectin | Over 90 Days |
| Injected with E. coli Solution | 1 Day |
| Injected with E. coli Solution + Soluble P-selectin | 3 Day |

Example 4

Platelet Aggregation Inhibition Test of Anthrax Lethal Toxin

The effect of anthrax lethal toxin on inhibiting coagulation was tested in the platelet aggregation test. Recombinant anthrax lethal toxin, which is obtained from a DNA synthesized by the artificial gene synthesizing technique in combination with PCR technique (Chang et al., 1993, Biochem. Biophys. Res. Commun. 190, 242-9), based on the DNA and protein information (AF065404 and NC_001496) obtained from NCBI Gene Bank, USA, was used as the anthrax lethal toxin.

Figure 3:
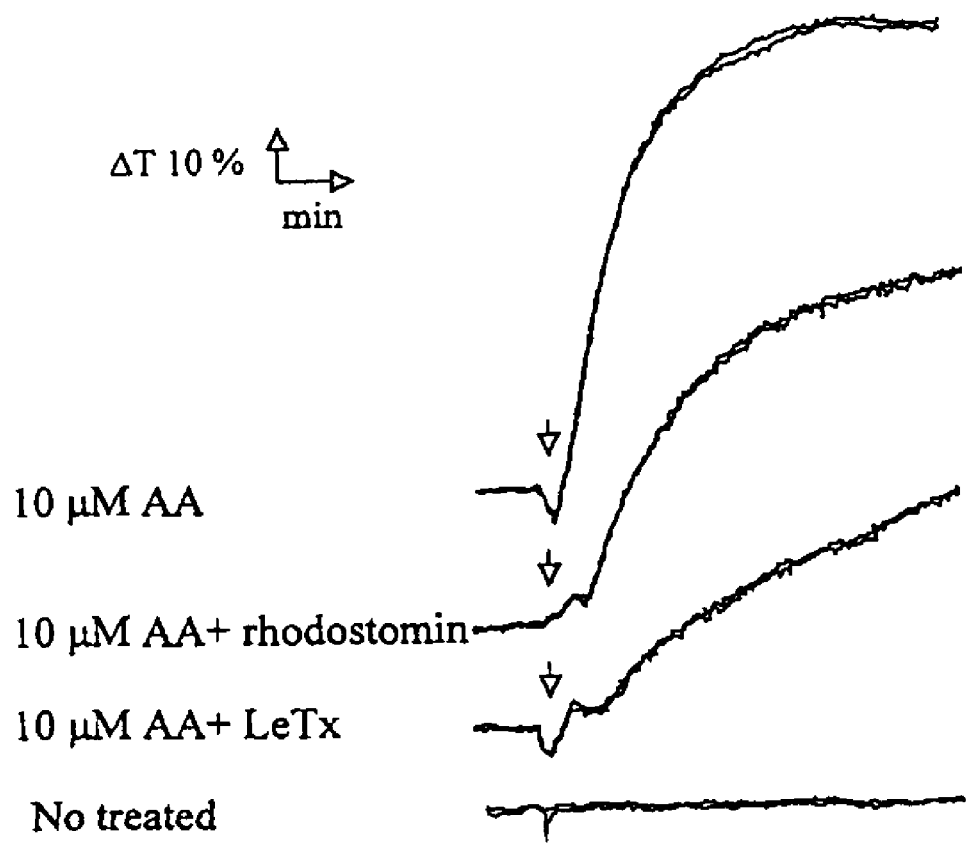
FIG. 3 shows the data of platelet aggregation inhibition of anthrax lethal toxin. The symbol "AA" in the figure means arachidonic acid and "LeTx" means anthrax lethal toxin.

Blood from mice (C57BL/6J) was centrifuged under 500×g for 10 minutes to obtain the "platelet-rich plasma" (PRP) of the mice. The platelet activator, arachidonic acid, was added to the obtained plasma, and the change in absorbance resulted from coagulation was recorded under stirring (800 rpm) and 37° C. on an aggregometer (Model 600B, Ion-Trace, Stouffville, Canada), and the plasma clotting time was determined. As shown in FIG. 3, after treatment with platelet activator, the purified platelets proceeded with normal aggregation. However, the experimental group added with anthrax lethal toxin showed inhibition. Therefore, anthrax lethal toxin can significantly inhibit platelet aggregation.

Example 5

Hemorrhage Shock Mouse Model of Ischemia/Reperfusion

The effect of soluble P-selectin in stabilizing blood pressure was tested in the hemorrhage shock mouse model of ischemia/reperfusion.

Mice were bled from their vein for about 40% of the total blood volume until their blood pressure lowered to 30-40 mmHg. After maintaining the blood pressure at 30-40 mmHg for 30 minutes, the mice were reperfused with recombinant P-selectin-Ig protein, P-selectin ligand-1 (PSGL-1), neutralizing monoclonal antibody, or control human immunoglobulin IgG (the dosages are all 1.2 µg/g). The changes in blood pressure and survival times of the mice were observed.

Figure 4:
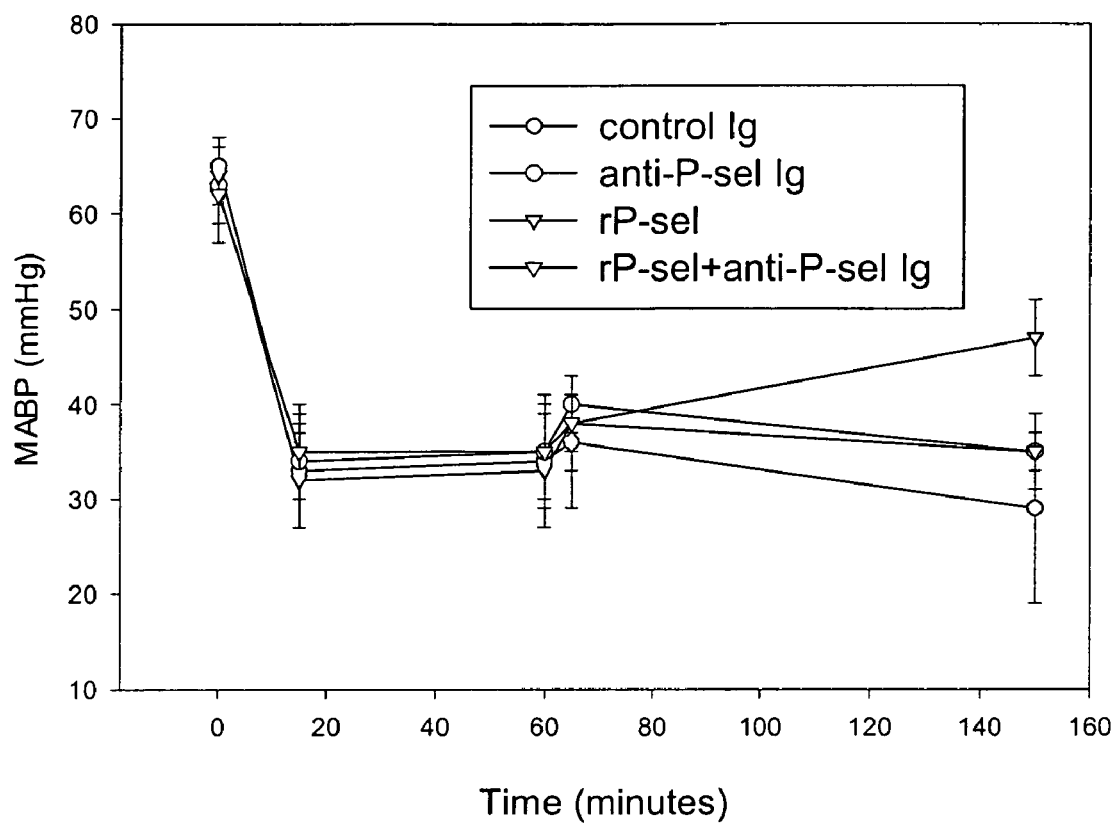
FIG. 4 shows the data obtained in the hemorrhage shock mouse model of ischemia/reperfusion. The symbol "-●-" means Control Immunoglobulin (Ig); the symbol "-○-" means Anti-P-selectin Antibody (Anti-P-sel); the symbol "-∇-" means Recombinant Soluble P-selectin (rP-sel); and the symbol "-∇-" means rP-sel+Anti-P-sel.

The results shown in FIG. 4 proved that soluble P-selectin can stabilize the low blood pressure resulted from loss of blood in the hemorrhage shock mouse model of ischemia/reperfusion. As shown in FIG. 4, the average blood pressure of the mice treated with soluble P-selectin is higher than that of the mice of the control group. On the other hand, anti-P-selectin antibodies or PSGL-1 can neutralize the blood-pressure-stabilizing effect of soluble P-selectin, and thus can be used as antagonists of soluble P-selectin.

Example 6

Hemorrhage Shock Mouse Model of Ischemia

The effect of soluble P-selectin in protecting hypoxic/ischemic tissues was tested in the hemorrhage shock mouse model of ischemia.

Mice were intravenously injected with control bovine serum albumin (BSA), soluble P-selectin, anti-P-selectin antibodies or PSGL-1. After 4 hours, the mice were bled from their vein for about 40% of the total blood volume until their blood pressure lowered to 30-40 mmHg. The blood pressure was maintained at 30-40 mmHg for 30 minutes. No reperfusion was given to the mice. The activity of caspase-3 in ischemic tissues was observed for 3 hours.

Figure 5:
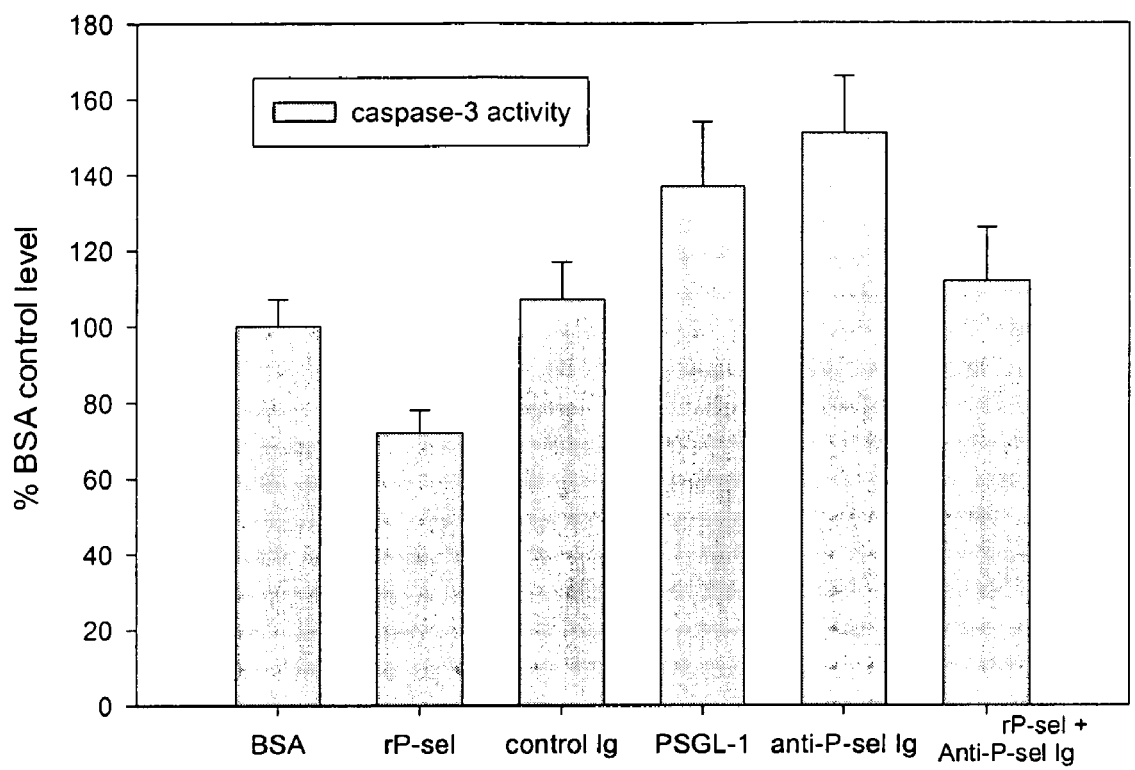
FIG. 5 shows the data obtained in the hemorrhage shock mouse model of ischemia. The bars in the figure represent, from left to right: Bovine Serum Albumin (BSA); Recombinant Soluble P-selectin (rP-sel); Control Immunoglobulin (Ig); P-selectin Ligand-1 (PSGL-1); Anti-P-selectin Antibody (Anti-P-sel); and rP-sel+Anti-P-sel.

As shown in FIG. 5, the mice pre-treated with soluble P-selectin had the lowest caspase-3 activity, followed by those pre-treated with BSA, and those mice pre-treated with anti-P-selectin antibodies or PSGL-1 had the highest caspase-3 activity. Such results proved that soluble P-selectin can help tissues against a hypoxic environment. On the other hand, anti-P-selectin antibodies or PSGL-1 antagonized the effect of soluble P-selectin.

Example 7

Clotting Analysis of Recombinant Proteins rP-sel and rPSGL-1 and Anti-P-sel-Ig Antibody Eight to ten weeks old C57BL/6 mice were used in the test. Recombinant proteins rP-sel and rPSGL-1 were derived form baculovirus expression system (BD Biosciences Clontech, Palo Alto, Calif., U.S.A.) to express the mouse P-sel and PSGL-1 cDNA-human IgG Fc cDNA fusion genes respectively (both contain human IgG Fc fusion). Anti-P-sel-Ig was prepared by rabbit hyperimmunized with recombinant P-sel (without human IgG Fc fusion) expressed in E. coli. The polyclonal antibody was first purified utilizing a protein-A column and then with an rP-sel affinity column. All related chemicals such as warfarin and buffers were purchased from Sigma-Aldrich, St. Louis, Mo., U.S.A.

Activated partial thromboplatin time (APTT) was employed to determine the inhibition of coagulant pathways using a coagulometer (model ACL Futura Plus, Instrumentation Laboratory, Milan, Italy) following the manufacturer's instructions. rP-sel, rPSGL-1 and anti-P-sel-Ig were introduced into experimental mice, only rP-sel could ameliorate the anti-coagulant drug Warfarin induced hemorrhage symptoms and mortality, by contrast, rPSGL-1 and anti-P-sel-Ig would greatly enhance the hemorrhage and mortality. The data showed that both rPSGL-1 and anti-P-sel-Ig treatments (24-36 hours) could prolong the plasma clotting time (APTT, activated partial thromboplatin time) and result in a hypocoagulable state in mice. Therefore rPSGL-1 and anti-P-sel-Ig not only could be applied in the P-sel blockage, but also to the therapeutic usages when a suppressed coagulant status is required in patients.

Example 8

Testing for Stabilization of Blood Pressure and Reduction of Expression Levels of Hypoxia-Inducing Factor 1α (HIF-1α)

Figure 6:
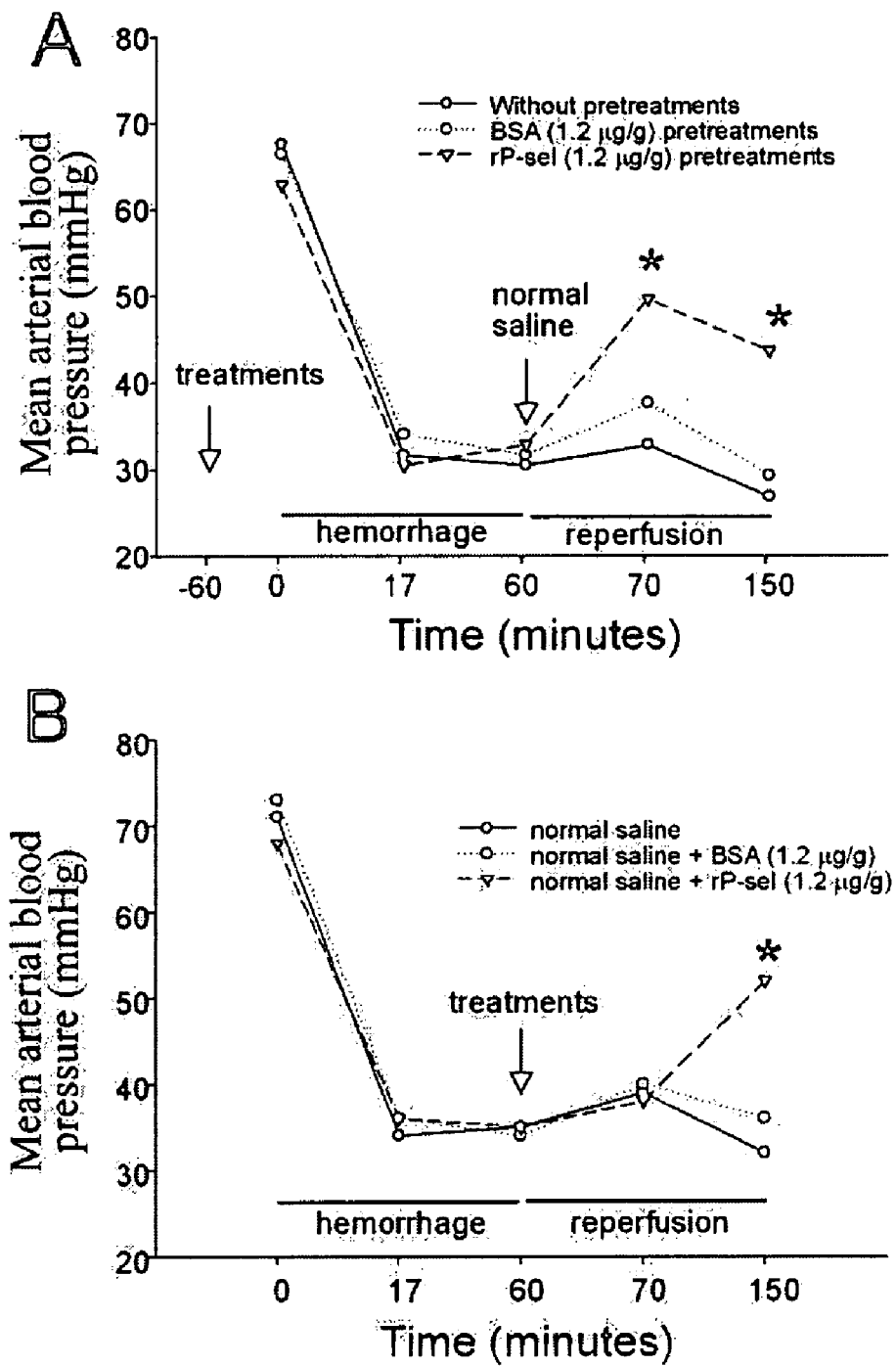
FIGS. 6A-6B show the mean arterial blood pressure (Y-axis) of mice during hemorrhage/reperfusion procedures. X-axis indicated the time (minutes) after blood collection. One hour after blood collection, normal saline (100 µl, 11/g, injected within 1 minutes) was perfused into these mice. Arrows indicated the time points of mice treated with bovine serum albumin (BSA, 1.2 µg/g), or rP-sel (1.2 µg/g), respectively, before (A) or after (B) the hemorrhage/reperfusion procedure. BSA was used as a negative control protein. * P value <0.05 as compared to both BSA and saline treated groups (n=8).

Using cannulation, arterial blood pressure of experimental mice (C57BL/6J) was recorded in a hemorrhage/reperfusion model. In this model, approximately 40% blood was drawn from the circulation of experimental mice for 60 minutes (maintaining blood pressure at 35 mmHg from 17 min to 60 min), and then normal saline (100 µl/g) was perfused into the mice. These mice will die several hours later after such treatments; blood pressure and the surviving time were recorded during the whole processes. The resulting data indicated that treatments of recombinant P-selection (rP-sel)(1.2 µg/g), both before and after hemorrhage/reperfusion procedures, significantly maintaining the mice blood pressure in a relatively higher level (as compared with BSA- or saline-treated control mice)(FIG. 6, n=8).

Figure 7:
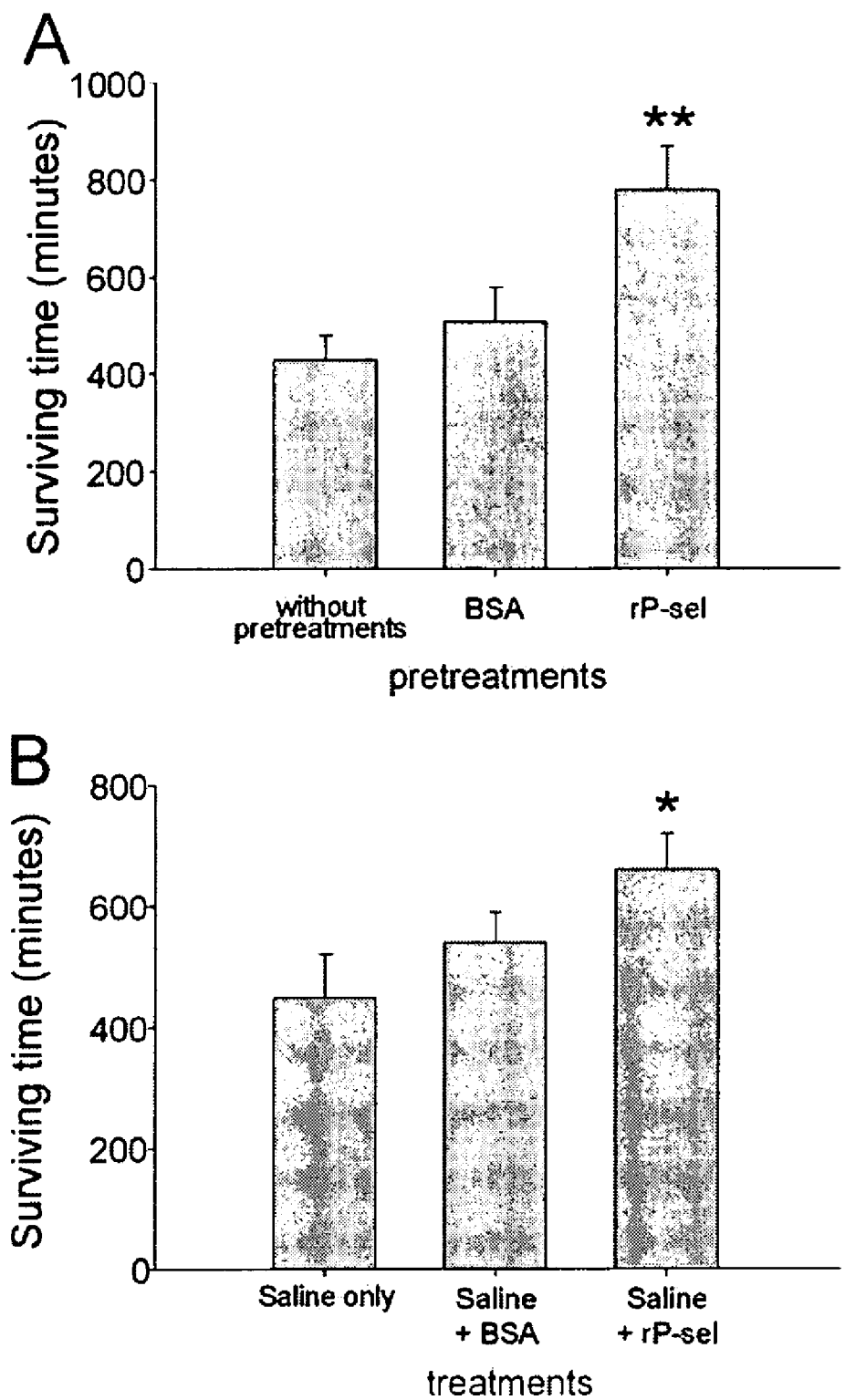
FIGS. 7A-B show the surviving time (minutes, Y-axis) of mice after hemorrhage/reperfusion procedures. X-axis indicated treatments before (A) or after (B) the blood collection. ** P value <0.01 as compared to "without pretreatments" groups in (A), * P value <0.05 as compared to "saline only" groups in (B), (n=4). All experimental procedures conducted here is equal to methods used FIG. 8.
Figure 8:
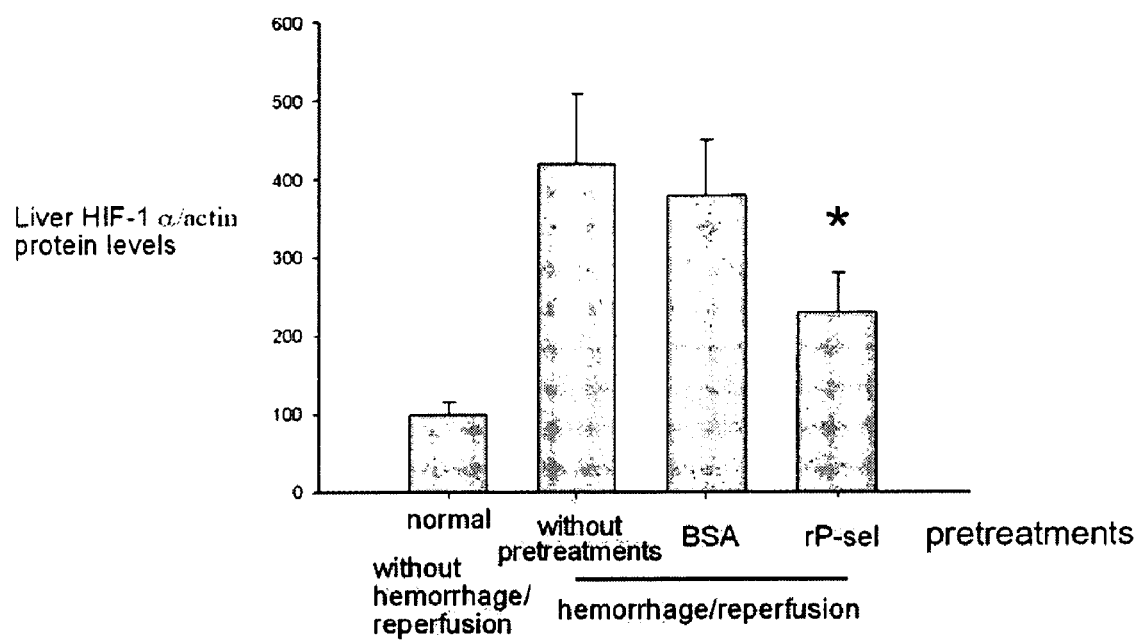
FIG. 8 shows the Protein expression levels of HIF-1α in liver of mice pretreated with or without BSA and rP-sel. Quantitative results were from Western blotting analysis. All HIF-1α levels were normalized with respective protein levels of actin, an internal control. * P<0.05, compared to both "without pretreatments" groups and BSA groups (n=3).

In addition, the surviving time of rP-sel treated mice was significantly increased (FIG. 7, n=8). Since pretreatments of rP-sel have a stronger protective effect than that of treated after hemorrhage, it is suggested that certain irreversible damages caused by ischemia and hypoxia during the delayed time could not totally been recovered by rP-sel treatments. Therefore, the protein expression levels of hypoxia-inducing factor 1α (HIF-1α), a marker for hypoxia, were further analyzed. The results of Western blotting indicated that, among all hemorrhage/reperfusion experimental groups, rP-sel treated groups showed lowest HIF-1α expression, which indicated that rP-sel treatments indeed ameliorate the ischemic damages through reducing the hypoxic stress (FIG. 8). The resulting data suggested that rP-sel treatments could help maintaining blood pressure in a relative normal state during ischemic situation. In addition, rP-sel treatments are also effective in preventing from ischemia- and hypoxia-induced damages, and whence prolonged the surviving time of ischemic mice. It is noteworthy that because there is no further bleeding of mice after the first blood collection, during the later hemorrhage/reperfusion procedures, thus the amelioration effect of rP-sel treatment is not contributed by its ability to enhance coagulation.

What is claimed is:

1. A method of reducing hypoxic stress in a mammal, which comprises administrating to said mammal a pharmaceutical composition comprising an effective amount of soluble P-selectin and a pharmaceutically acceptable carrier.

2. The method according to claim 1, wherein the soluble P-selectin is selected from the group consisting of naturally occurring soluble P-selectin, and recombinant forms thereof.

3. The method according to claim 1, wherein the pharmaceutical composition is administered via intravenous injection.

4. The method according to claim 1, wherein the soluble P-selectin is administered at an amount of about 0.1 ng to about 100 mg per kilogram of bodyweight.

* * * * *